United States Patent [19]

Goudar

[11] Patent Number: 5,965,742
[45] Date of Patent: *Oct. 12, 1999

[54] SELECTIVE CHLORINATION OF A 1-(2-FLUOROPHENYL)-1,2,4-TRIAZOLE

[75] Inventor: Jaidev S. Goudar, Plainsboro, N.J.

[73] Assignee: FMC Corporation, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 09/091,867

[22] PCT Filed: Nov. 20, 1996

[86] PCT No.: PCT/US96/18600

§ 371 Date: Jun. 25, 1998

§ 102(e) Date: Jun. 25, 1998

[87] PCT Pub. No.: WO97/24337

PCT Pub. Date: Jul. 10, 1997

Related U.S. Application Data

[60] Provisional application No. 60/009,320, Dec. 29, 1995.

[51] Int. Cl.$^6$ .................................................. C07D 249/12
[52] U.S. Cl. ............................................................ 548/263.2
[58] Field of Search ........................................... 548/263.2

[56] References Cited

U.S. PATENT DOCUMENTS 5,468,868 11/1995 Halfon et al. ........................ 548/263.2

*Primary Examiner*—Patricia L. Morris
*Attorney, Agent, or Firm*—FMC Corporation

[57] ABSTRACT

A process is disclosed in which the 4-position of the 1-(2-fluorophenyl) group attached to a 4,5-dihydro-3-methyl-5-oxo-1H-1,2,4-triazole, an intermediate in the route to prepare the herbicide ethyl α-2-dichloro-5-[4-(difluoromethyl)-4,5-dihydro-3-methyl-5-oxo-1H-1,2,4-triazol-1-yl]-4-fluorobenzenepropanoate, is chlorinated in good yield. The process involves adding chlorine gas in three separate steps, with by-product hydrogen chloride being removed at the end of each chlorine addition step.

13 Claims, No Drawings

SELECTIVE CHLORINATION OF A 1-(2-FLUOROPHENYL)-1,2,4-TRIAZOLE

This application is a 371 national stage application of PCT/US96/18600, filed Nov. 20, 1996, which claims the benefit of U.S. Provisional Application No. 60/009,320, filed Dec. 29, 1995.

The present invention relates to the chlorination of a phenyl ring. In particular it discloses a method by which a chlorine atom is placed in the 4-position of the 1-(2-fluorophenyl) group attached to a 4,5-dihydro-3-methyl-5-oxo-1H-1,2,4-triazole, an intermediate in the route to prepare the herbicide ethyl α-2-dichloro-5-[4-(difluoromethyl)-4,5-dihydro-3-methyl-5-oxo-1H-1,2,4-triazol-1-yl]-4-fluorobenzenepropanoate (the "Target Herbicide").

Early attempts to achieve an efficient preparation of the Target Herbicide focused on the method taught in U.S. Pat. No. 4,818,275 in Example 1, in which 1-(5-amino-2-fluoro-4-chlorophenyl)-4-difluoromethyl-4,5-dihydro-3-methyl-5-oxo-1H-1,2,4-triazole was prepared in an eight-step route from 2-fluoroaniline. In this process the chlorination of the phenyl ring in the 4-position is accomplished before ring closure to the triazole ring by reacting 2-fluoroacetanilide with sulfuryl chloride in p-dioxane. However, it soon became apparent that this eight step route would not be satisfactory, owing to the excessive number of steps to and poor overall yields.

While the efficiency of a multistep process to prepare a complex molecule can be improved by optimizing the yield of each step, even greater efficiency may be achieved by finding a route with fewer steps. It has now been found that the Target Herbicide may be prepared more efficiently by a new route in which there are only six steps. In the first step 2-fluorohydrazine is cyclized to 4,5-dihydro-1-(2-fluorophenyl)-3-methyl-5-oxo-1H-1,2,4-triazole, which is then chlorinated to 1-(4-chloro-2-fluorophenyl)-4,5-dihydro-3-methyl-5-oxo-1H-1,2,4-triazole. In the third step the chlorinated product is difluoromethylated, affording 1-(4-chloro-2-fluorophenyl)-4-difluoromethyl-4,5-dihydro-3-methyl-5-oxo-1H-1,2,4-triazole. In an alternative, less preferred method, 4,5-dihydro-1-(2-fluorophenyl)-3-methyl-5-oxo-1H-1,2,4-triazole may first be difluoromethylated and then chlorinated. The third step intermediate is nitrated, yielding 1-(4-chloro-2-fluoro-5-nitrophenyl)-4-difluoromethyl-4,5-dihydro-3-methyl-5-oxo-1H-1,2,4-triazole, which is reduced to the corresponding 1-(5-amino-4-chloro- 2-fluorophenyl)-4-difluoromethyl-4,5-dihydro-3-methyl-5-oxo-1H-1,2,4triazole. In the final step the 5-amino derivative is subjected to diazotization/arylation, yielding the Target Herbicide.

The present invention is directed to the preparation of a key intermediate in this process, the product of the second step, 1-(4-chloro-2-fluorophenyl)-4,5-dihydro-3-methyl-5-oxo-1H-1,2,4-triazole, which is prepared in surprisingly good yield by the chlorination of 4,5-dihydro-1-(2-fluorophenyl)-3-methyl-5-oxo-1H-1,2,4-triazole by the novel process here disclosed and claimed. In the alternative, but less desirably, the chlorination reaction may be carried out on the potassium salt of the starting material.

When the six-step process outlined above, was first considered, it was thought that the chlorination of 4,5-dihydro-1-(2-fluorophenyl)-3-methyl-5-oxo-1H-1,2,4-triazole in good yield would be difficult to accomplish on a large scale. Attempts to chlorinate 4,5-dihydro-1-(2-fluorophenyl)-3-methyl-5-oxo-1H-1,2,4-triazole with sulfuryl chloride, the chlorinating agent used in the analogous chlorination in the eight-step process, were unsatisfactory, giving very low yields. For example, in one experiment the yield, as determined by gas chromatography (GC), was only about 8 area percent after 18 hours. (In the chlorination reactions reported here, area percent does not represent actual yield of product, since it does not allow for by-products not detectable by GC. However, it is an indication of the extent to which the reaction has progressed, i.e., the percent conversion of starting material.) Early attempts at chlorination with elemental chlorine in the laboratory gave actual yields in the order of seventy percent, even with a substantial molar excess of chlorine. The reaction was not deemed suitable for running in the pilot plant.

Surprisingly, it has now been found that chlorination of 4,5-dihydro-1-(2-fluorophenyl)-3-methyl-5-oxo-1H-1,2,4-triazole with three separate feeds of about one molar equivalent each of chlorine gas, and subsequent removal of the by-product hydrogen chloride between feeds, consistently provides actual yields of 4,5-dihydro-1-(4-chloro-2-fluorophenyl)-3-methyl-5-oxo-1H-1,2,4-triazole of 82–87% in the laboratory, 75 to 80% or higher in the pilot plant (up to about 97% conversion), at a purity of 95% or better.

In the process of this invention a total of three molar equivalents of elemental chlorine is fed into the reaction mixture in three separate charges of approximately one equivalent each. Typical conversions to predominantly 1-(4-chloro-2-fluorophenyl)-4,5-dihydro-3-methyl-5-oxo-1H-1,2,4-triazole after each of the three feeds of chlorine are, in area percent, about 50%, 75%, and greater than 97%, respectively.

The key to these superior yields is the removal of the hydrogen chloride gas generated during the chlorination steps after each of the one molar equivalent chlorine feeds. If left in the reaction mixture, the hydrogen chloride will stall the reaction and/or react with the acetonitrile solvent, thereby giving reduced yields of product. The hydrogen chloride is removed from the reaction mixture to the extent possible by first using a vacuum strip, then optionally purging with nitrogen. The reduced hydrogen chloride concentration also helps to reduce the corrosivity of the reaction mixture, which becomes especially important during the reaction, filtration, and handling steps. In the preferred process of the present invention, 4,5-dihydro-1-(2-fluorophenyl)-3-methyl-5-oxo-1H-1,2,4-triazole (one equiv.) is placed in a solvent such as acetonitrile, N,N-dimethylformamide, nitromethane, or nitrobenzene, preferably acetonitrile. The concentration of this 2-fluorophenyl derivative in the solvent on a percent weight of 2-fluorophenyl derivative to volume of solvent is in the range of about 5 to 70%, preferably about 10 to 35%, and most preferably 15 to 25%. The solvent used may be fresh, recycled from previous runs of this chlorination reaction, or combinations of fresh and recycled. The resulting slurry is stirred during the chlorination steps at a temperature in the range of about 0° C. to about 75° C., preferably ambient temperature (e.g., 23° C.) to 50° C., and most preferably 30° C. to 40° C. In a pilot plant scale run of the process of the present invention, the chlorine addition is conducted in a closed system under a vacuum of about 300 to 500 mm Hg, which helps to alleviate pressure build-up from the chlorine gas addition. Laboratory scale runs of the chlorination are routinely conducted at atmospheric pressure with no apparent adverse consequence. The chlorine gas feed rate is important to ensure proper absorbtion. In a pilot plant scale run, the reactor pressure is dependent on the rate of chlorine gas addition versus the rate of reaction. It is preferred to maintain the pressure in the reactor under 15 psig by the rate of addition of chlorine gas, preferably, at about 0.5 lb/minute. With the reaction mixture in the preferred temperature range, 0.8 to 1.6 molar equivalents, preferably 0.9 to 1.5 molar equivalents, of chlorine gas are added below the surface of the reaction mixture at a rate that will maintain the reaction mixture below 50° C., preferably between 30° C. and 40° C. The time required to complete the first feed of chlorine gas while maintaining the above conditions is about 10 minutes to two hours, preferably 20 minutes to one hour. Upon completion of the first feed of chlorine gas the reaction mixture is brought to a temperature of about 30° C. to 50° C., preferably 30° C. to 40° C., where it is stirred for a hold time of one to 10 hours, preferably three to six hours, after which time the conversion of 4,5-dihydro-1-(2-fluorophenyl)-3-methyl-5-oxo-1H-1,2,4-triazole to 1-(4-chloro-2-fluorophenyl)-4,5-dihydro-3-methyl-5-oxo-1H-1,2,4-triazole, as determined by gas chromatographic methods, is about 50% (area %). Upon completion of the hold-time the reaction mixture is maintained at the preferred temperature of 30° C. to 40° C. and placed under reduced pressure. In a pilot plant scale run the pressure reduction is to about 100 to 200 mm Hg, preferably 135 to 165 mm Hg. In a laboratory scale run, the pressure reduction is to about 10 to 30 mm Hg, preferably 15 to 25 mm Hg. In a pilot plant scale run, refluxing under the conditions described above is continued for a period of one to six hours, preferably two to four hours during which time trace amounts of residual chlorine and about 99% of the by-product hydrogen chloride is driven off. If more than 1% of the hydrogen chloride remains in the reaction mixture, the reaction mixture is purged with nitrogen gas to bring the hydrogen chloride level to less than 1%. In a laboratory scale run, refluxing under the conditions described above is continued for a period of about 20 minutes to two hours, preferably 30 to 50 minutes, then the reaction mixture is purged with nitrogen gas for a period of about 10 to 30 minutes, preferably 15 to 25 minutes. Upon completion of the first feed of chlorine gas and the subsequent removal of the by-product hydrogen chloride, the process is repeated with a second feed of chlorine gas in the amounts and under the conditions described above. The conversion of 4,5-dihydro-1-(2-fluorophenyl)-3-methyl-5-oxo-1H-1,2,4-triazole to 1-(4-chloro-2-fluorophenyl)-4,5-dihydro-3-methyl-5-oxo-1H-1,2,4-triazole after the second feed, as determined by gas chromatographic methods, is about 75% (area %). The subsequent removal of the by-product hydrogen chloride is again conducted under conditions described above. A third feed of chlorine and by-product hydrogen chloride removal are conducted in the same manner. Upon completion of the third feed of chlorine and the subsequent by-product hydrogen chloride removal, conversion of 4,5-dihydro-1-(2-fluorophenyl)-3-methyl-5-oxo-1H-1,2,4-triazole to 1-(4-chloro-2-fluorophenyl)-4,5-dihydro-3-methyl-5-oxo-1H-1,2,4-triazole, as determined by gas chromatographic methods, is about 97% (area %) or better. After removal of the hydrogen chloride the reaction mixture is cooled and the solid product collected by filtration or centrifugation. In a pilot plant scale run, the reaction mixture is cooled to about 0° C. to 15° C., preferably to 3° C. to 10° C. to maximize precipitation of any product in solution, and held at this temperature for about 30 minutes to two hours, preferably one hour. The solid product is collected by centrifugation and washed with a cold solvent, preferably acetonitrile. In the pilot plant scale runs, yields of 1-(4-chloro-2-fluorophenyl)-4,5-dihydro-3-methyl-5-oxo-1H-1,2,4-triazole are about 80% with purity of 98 to 100%. In corresponding laboratory scale runs, yields of 82% to 89% are obtained with purity of 98 to 100%. The acetonitrile solvent removed from the product by filtration or centrifugation may be distilled for use in subsequent chlorinations by this process.

Attempts to catalyze the chlorination steps described above with a variety of catalysts failed to significantly enhance the rate of reaction or to drive it any further to completion. Catalysts tried included p-toluenesulfonic acid, ytterbium trifluoromethanesulfonate, acetic acid, hydroxy (4-methylbenzenesulfonato-O)phenyl iodine, triethyl phosphite, water, sulfuric acid, 2,6-di-tert.-butyl-4-methylphenol, elemental iodine, tris[2-(2-methoxyethoxy) ethyl]amine, aluminum chloride, tetrabutylammonium chloride, tetrabutylammonium bromide, dimethylamino-pyridine, and ferric chloride. A number of basic reagents were also tried in stoichiometric amounts to scavenge the by-product hydrogen chloride. These included sodium acetate, poly(4-vinyl)pyridine, triethylamine, and 1,8-diazabicyclo-[5.4.0]undec-7-ene. Although the reagents neutralized the hydrogen chloride produced, none of them significantly enhanced the rate of reaction or drove the reaction any further to completion.

Chlorination by methods generally as described above were conducted with the potassium salt of 4,5-dihydro-1-(2-fluorophenyl)-3-methyl-5-oxo-1H-1,2,4-triazole or with 4-difluoromethyl-4,5-dihydro-1-(2-fluorophenyl)-3-methyl-5-oxo-1H-1,2,4-triazole. These reactions generally did not proceed as rapidly as did the preferred 4,5-dihydro-1-(2-fluorophenyl)-3-methyl-5-oxo-1H-1,2,4-triazole, although both species yielded the corresponding chlorinated product. The series of chlorination reactions that used 4-difluoromethyl-4,5-dihydro-1-(2-fluorophenyl)-3-methyl-5-oxo-1H-1,2,4-triazole required an excessive amount of chlorine and prolonged reaction times to drive the reaction to its completion. A number of the catalysts listed above were used to in an attempt to enhance the rate of reaction, but failed to have any effect.

Specific examples of the application of the process of the invention are given below.

EXAMPLE 1

PREPARATION OF 1-(4-CHLORO-2-FLUOROPHENYL)-4,5-DIHYDRO-3-METHYL-5-OXO-1H-1,2,4-TRIAZOLE BY THE CHLORINATION OF 4,5-DIHYDRO-1-(2-FLUOROPHENYL)-3-METHYL-5-OXO-1H-1,2,4-TRIAZOLE

Laboratory Scale

A 1500 mL reaction vessel equipped with a mechanical stirrer, temperature probe, a gas inlet tube, and a condenser was charged with 200 grams (1.035 mole; 1.0 equiv.) of 4,5-dihydro-1-(2-fluorophenyl)-3-methyl-5-oxo-1H-1,2,4-triazole and 1006 mL of acetonitrile (wt. %/vol.—triazole/ solvent is 19.88%). The stirred mixture was purged with nitrogen for about 25 minutes; then the temperature was brought to 35° C. Chlorine gas, about 73.7 grams (1.035 mole; one equiv.), was then bubbled in below the surface of the reaction mixture during a one hour period. Upon completion of the addition the reaction mixture was stirred at 35° C. for about six hours, at which time gas chromatographic (GC) analysis of the reaction mixture indicated the reaction had progressed to about 50% (area %) conversion to product. While the temperature was maintained at 35° C., the reaction mixture was placed under a vacuum of about 20 mm Hg for 45 minutes to remove the by-product hydrogen chloride. The reaction mixture was then purged for 20 minutes with nitrogen gas to further remove by-product hydrogen chloride. Upon removal of the hydrogen chloride the reaction mixture was allowed to cool to ambient temperature, where it stirred for about 16 hours. (This length of time was for convenience, not necessity, only about three hours are required.) After this time a second equivalent of 73.7 grams (1.035 mole; one equiv.) of chlorine gas was bubbled in below the surface of the reaction mixture during a one hour period. Upon completion of the addition the reaction mixture was brought to 35° C., where it stirred for 1.5 hours, at which time GC analysis indicated the reaction had progressed to about 75% (area %) conversion to product. With the temperature still held at 35° C., the reaction mixture was again placed under a vacuum of about 20 mm Hg for one hour to remove the by-product hydrogen chloride. The reaction mixture was again purged for 20 minutes with nitrogen gas to further remove by-product hydrogen chloride. Upon removal of the hydrogen chloride the reaction mixture was allowed to cool to ambient temperature, where it stirred for about 16 hours (again, as a matter of convenience). After this time a third equivalent of 73.7 grams (1.035 mole; one equiv.) of chlorine gas was bubbled in below the surface of the reaction mixture during a period of one hour. Upon completion of the addition the reaction mixture was brought to 35° C., where it was again stirred for six hours, at which time GC analysis indicated the reaction had progressed to about 97% (area %) conversion to product. With the temperature still held at 35° C., the reaction mixture was again placed under a vacuum of about 20 mm Hg for one hour to remove the byproduct hydrogen chloride. The reaction mixture was then purged for 30 minutes with nitrogen gas to further remove hydrogen chloride, cooled to ambient temperature, and filtered to yield a first crop of 184.5 grams of solid product. Distillation of the mother liquor under vacuum at about 5 mm Hg without heat yielded 936.5 mL of acetonitrile (93.1% recovery). A second crop of 2.3 grams of product was collected from the pot residue remaining from the distillation. The two crops of product were combined, yielding 186.8 grams of (83.5% yield) of 1-(4-chloro-2-fluorophenyl)-4,5-dihydro-3-methyl-5-oxo-1H-1,2,4-triazole which was 99.5% pure (weight % as determined by gas chromatographic methods).

EXAMPLE 2

PREPARATION OF 1-(4-CHLORO-2-FLUOROPHENYL)-4,5-DIHYDRO-3-METHYL-5-OXO-1H-1,2,4-TRIAZOLE BY THE CHLORINATION OF 4,5-DIHYDRO-1-(2-FLUOROPHENYL)-3-METHYL-5-OXO-1H-1,2,4-TRIAZOLE

50 Gallon Pilot Plant Scale

A 50 gallon glass-lined reaction vessel equipped with a Hasteloy condenser and a glass stirring device was charged with 115 pounds of acetonitrile recycled from a previous run of the present reaction, 47.4 pounds of fresh acetonitrile (total 162.4 pounds—94.685 liters), and 40.6 pounds (0.210 lb-mole; 1.00 equiv.—18.416 Kg) of 4,5-dihydro-1-(2-fluorophenyl)-3-methyl-5-oxo-1H-1,2,4-triazole (wt. %/vol.—triazole/solvent is 19.46%). The mixture was then stirred and warmed to 35° C. During the warm-up period the reaction vessel was purged three times with nitrogen gas and sealed under a vacuum of about 300 to 500 mm Hg. Chlorine gas, 21.01 pounds (0.296 lb-mole; 1.41 equiv.) was then fed into the reaction mixture below the surface at a rate (about 0.5 lb./min.) to maintain the reaction mixture temperature at 40° C. or less and the reaction vessel pressure under 15 psig. The time required to complete the feed of chlorine gas was about 30 minutes. The chlorine gas feed lines were purged with nitrogen following the feed of chlorine, which caused some reduction in temperature. The reaction mixture temperature was then brought slowly to 40° C., while the reaction vessel pressure was kept under 15 psig. The reaction mixture was then stirred for a hold time of three hours, after which time it was analyzed for conversion of starting material to product and hydrogen chloride by-product content. During the three hour hold time the conversion of starting material to product, as determined by gas chromatographic methods, was about 50% (area %). After this time the reaction mixture was refluxed for three hours at 40° C./150 mm Hg, causing the removal of hydrogen chloride by-product. An acceptable hydrogen chloride by-product content of less than 1% had been achieved by the end of the three hour reflux. The reaction mixture was then cooled to 35° C., and the reaction vessel was placed under a vacuum of about 300 to 500 mm Hg. A second feed of chlorine gas, 14.01 pounds (0.198 lb-mole; 0.94 equiv.) was then charged (~seven hours following the first feed) into the reaction mixture in the manner described for the first feed of chlorine. The time required to complete the second feed of chlorine gas was about 30 minutes. Upon completion of the feed of chlorine, the reaction mixture was held at 40° C./≦15 psig for a three hour hold time, as previously described. The reaction mixture was then analyzed for conversion of starting material to product and hydrogen chloride by-product content. During the three hour hold time the conversion of starting material to product, as determined by gas chromatographic methods, was about 75% (area %). The reaction mixture was again refluxed for three hours at 40° C./150 mm Hg, to remove hydrogen chloride by-product to less than 1%. The reaction mixture was then adjusted to the conditions previously described, and a third feed of 14.01 pounds (0.198 lb-mole; 0.94 equiv.) of chlorine gas was charged (~14.5 hours following the first feed). Upon completion of the addition of the third feed of chlorine gas the reaction mixture was again held at 40° C. for four hours. A conversion of starting material to product of 96% (area %) or greater was accomplished during the four hour hold time. The reaction mixture was again refluxed at 40° C./≦15 psig for three hours to remove hydrogen chloride by-product. Upon completion of the reflux time (total reaction time: ~22.5 hours) the reaction mixture was cooled to 5° C. during 30 minutes, and stirred at that temperature for one hour. The reaction mixture was then transferred into an appropriate centrifuge, where it was spun for 30 minutes to remove the mother liquor. The mother liquor was placed in a separate receiver for reclamation of the acetonitrile by distillation. The filter cake was washed first with 35 pounds of cold (0–5° C.) acetonitrile charged directly into the centrifuge. The mixture was spun for 30 minutes to remove the acetonitrile wash. A second 35 pounds of cold acetonitrile was charged into the reaction vessel, where it was stirred for five minutes to remove any remaining reaction mixture. The acetonitrile wash was then transferred into the centrifuge, where it was spun as previously described. The filter cake was removed from the centrifuge and dried at 60° C./25 mm Hg for 24 hours, yielding 38.27 pounds (80.2% yield) of 1-(4-chloro-2-fluorophenyl)-4,5-dihydro-3-methyl-5-oxo-1H-1,2,4-triazole, which was 99.9% pure (weight % as determined by gas chromatographic methods).

I claim:

1. A process for the chlorination of 1-(2-fluorophenyl)-4,5-dihydro-3-methyl-5-oxo-1H-1,2,4-triazole (the "2-fluorophenyl compound") in the 4-position of the phenyl ring which comprises a) adding 0.8 to 1.6 molar equivalents of chlorine to a stirred slurry of 1-(2-fluorophenyl)-4,5-dihydro-3-methyl-5-oxo-1H-1,2,4-triazole in a solvent selected from acetonitrile, N,N-dimethylformamide, nitromethane, and nitrobenzene, at a temperature in the range of ambient to 50° C., at a rate such that the temperature does not exceed 50° C., and continuing the stirring at 30 to 50° C. for from one to ten hours;

b) for a period of from one to six hours, while maintaining the temperature at 30 to 50° C., reducing the pressure in the reaction vessel so that the solvent refluxes and most of the hydrogen chloride by-product is driven off;

c) optionally, purging the reaction vessel with nitrogen to reduce the hydrogen chloride concentration in the reaction mixture to below 1%;

d) repeating steps a, b, and c two times;

e) recovering 1-(4-chloro-2-fluorophenyl)-4,5-dihydro-3-methyl-5-oxo-1H-1,2,4-triazole.

2. A process of claim 1 which comprises a) adding 0.9 to 1.5 molar equivalents of chlorine to a stirred slurry of the 2-fluorophenyl compound in acetonitrile, the weight percent of the 2-fluorophenyl compound per volume of acetonitrile being in the range of 5 to 70%, at a temperature in the range of 30° C. to 40° C., at a rate such that the temperature is between 35 and 40° C., and continuing the stirring at 30 and 40° C. for from three to six hours;

b) for a period of from two to four hours, while maintaining the temperature at 35 and 40° C., reducing the pressure in the reaction vessel so that the solvent refluxes and most of the hydrogen chloride by-product is driven off.

3. A process of claim 2 in which steps a through d are carried out at reduced pressure.

4. A process of claim 3 in which the reduced pressure is in the range of 300 to 500 mm of mercury.

5. A process for chlorination of 1-(2-fluorophenyl)-4,5-dihydro-3-methyl-5-oxo-1H-1,2,4-triazole at the 4-position of the phenyl ring which comprises the steps of:

(a) adding chlorine to a mixture of 1-(2-fluorophenyl)-4,5-dihydro-3-methyl-5-oxo-1H-1,2,4-triazole and a solvent, wherein said addition forms hydrogen chloride as a by-product; and (b) reducing the concentration of the hydrogen chloride by-product after said addition.

6. The process of claim 5, wherein steps (a) and (b) are each performed three times in sequential order.

7. The process of claim 5, wherein said chlorine is added in step (a) in an amount of about 0.8 to about 1.6 molar equivalents.

8. The process of claim 6, wherein said chlorine is added in each step (a) in an amount of about 0.8 to about 1.6 molar equivalents.

9. The process of claim 5, wherein said solvent is selected from the group consisting of acetonitrile, N,N-dimethylformamide, nitromethane and nitrobenzene.

10. The process of claim 5, wherein said chlorine is added in step (a) at a temperature in the range of about ambient to about 50 C and at a rate such that the temperature does not exceed about 50 C.

11. The process of claim 9, wherein said solvent is acetonitrile.

12. The process of claim 6, wherein said solvent is selected from the group consisting of acetonitrile, N,N-dimethylformamide, nitromethane and nitrobenzene.

13. The process of claim 12, wherein said chlorine is added in step (a) at a temperature in the range of about ambient to about 50 C and at a rate such that the temperature does not exceed about 50C.

* * * * *